United States Patent
Sokal et al.

[11] Patent Number: 6,125,850
[45] Date of Patent: *Oct. 3, 2000

[54] VAGINAL DEVICE

[75] Inventors: David C. Sokal, Mebane; Laneta J. Dorflinger, Durham, both of N.C.; J. V. Tapani Luukkainen, Espoo, Finland; Parthena M. Martin, Chapel Hill, N.C.

[73] Assignee: Family Health International, Durham, N.C.

[*] Notice: This patent is subject to a terminal disclaimer.

[21] Appl. No.: 09/170,447

[22] Filed: Oct. 13, 1998

Related U.S. Application Data

[63] Continuation-in-part of application No. 08/960,898, Oct. 30, 1997, Pat. No. 5,819,742.
[60] Provisional application No. 60/030,361, Nov. 6, 1996.

[51] Int. Cl.[7] .................................................. A61F 6/06
[52] U.S. Cl. ............................................ 128/830; 128/832
[58] Field of Search ..................................... 128/830–841

[56]          References Cited
           U.S. PATENT DOCUMENTS

| | | | |
|---|---|---|---|
| 3,780,730 | 12/1973 | Weisman | 128/832 |
| 4,360,013 | 11/1982 | Barrows | 128/832 |
| 4,788,060 | 11/1988 | Endicott | 424/443 |
| 4,848,572 | 7/1989 | Herrera | 206/440 |
| 5,201,326 | 4/1993 | Kubicki | 128/832 |
| 5,819,742 | 10/1998 | Sokal | 128/830 |

*Primary Examiner*—Michael A. Brown
*Attorney, Agent, or Firm*—Richard S. Faust

[57]          ABSTRACT

A vaginal device provides physical and chemical barriers to contraception or protection against sexually transmitted diseases, or both. The device includes a towelette having approximately 1 to 10 ml of preventive formulation incorporated therein by absorption. During intercourse, the towelette rests in the upper vagina and effectively functions as both a physical and chemical barrier to contraception. In some embodiments, the towelette may become compressed into a crumpled, disc-like shape, which may enhance its properties as a physical barrier. In other embodiments, the vaginal device includes a flexible ring that is affixed to the towelette to define a dome-shaped towelette portion on one side of the ring and a depending skirt on the other side, with the dome portion being designed to cover the cervix. Means to facilitate insertion and removal of the device are described. In alternative embodiments, the vaginal device may incorporate a therapeutic formulation for treatment of vaginal conditions such as vaginal candidiasis, trichomoniasis and bacterial vaginosis or for delivering medication intended for systemic administration.

23 Claims, 12 Drawing Sheets

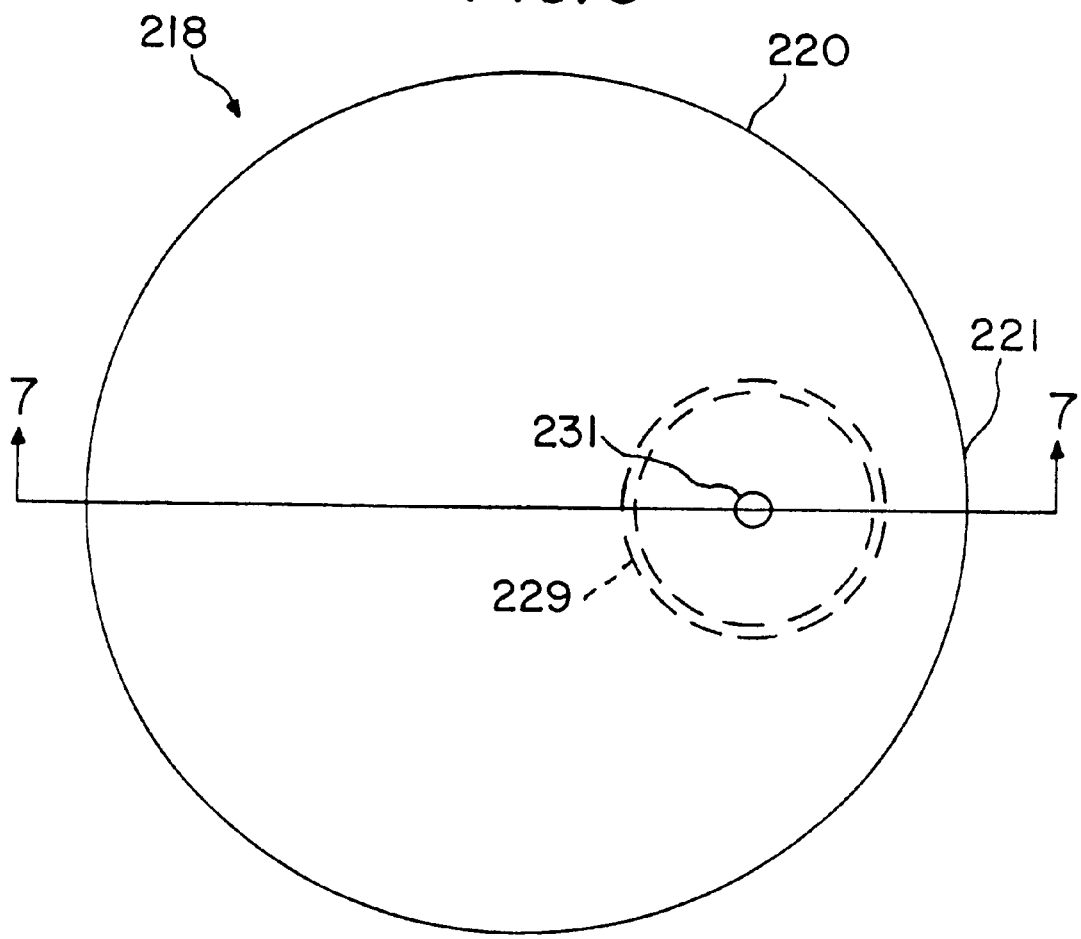
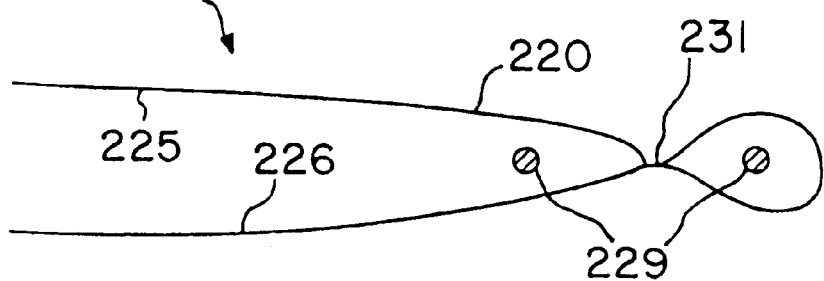

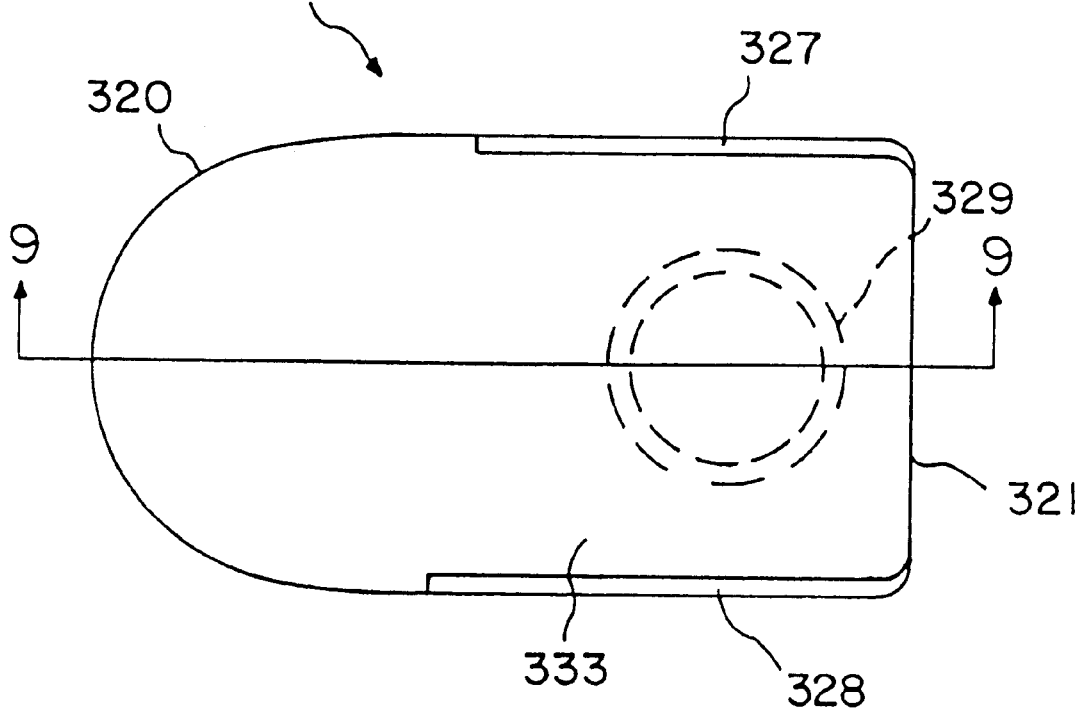
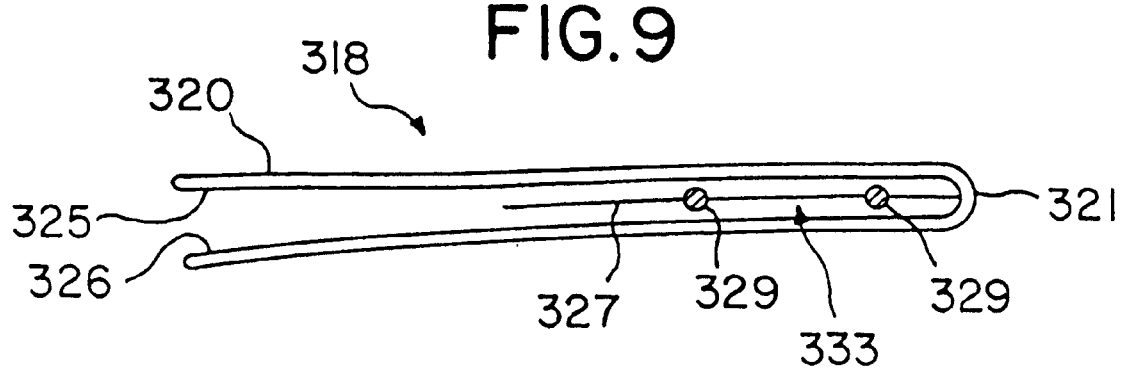

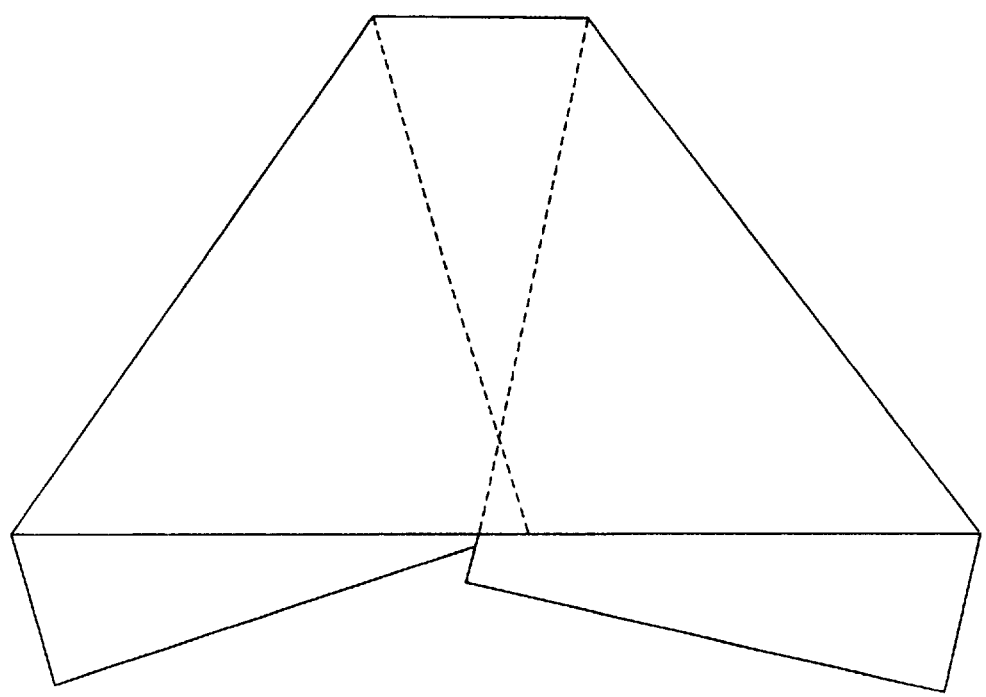
FIG. 16B
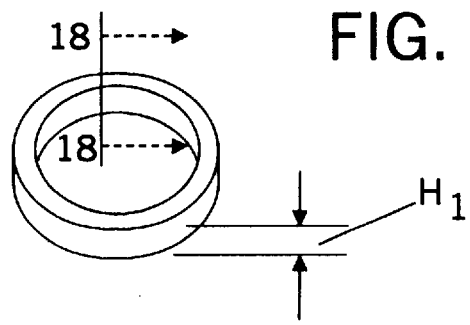
FIG. 17
FIG. 18A
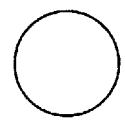
FIG. 18B
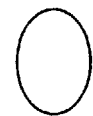
FIG. 18C
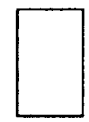
FIG. 18D

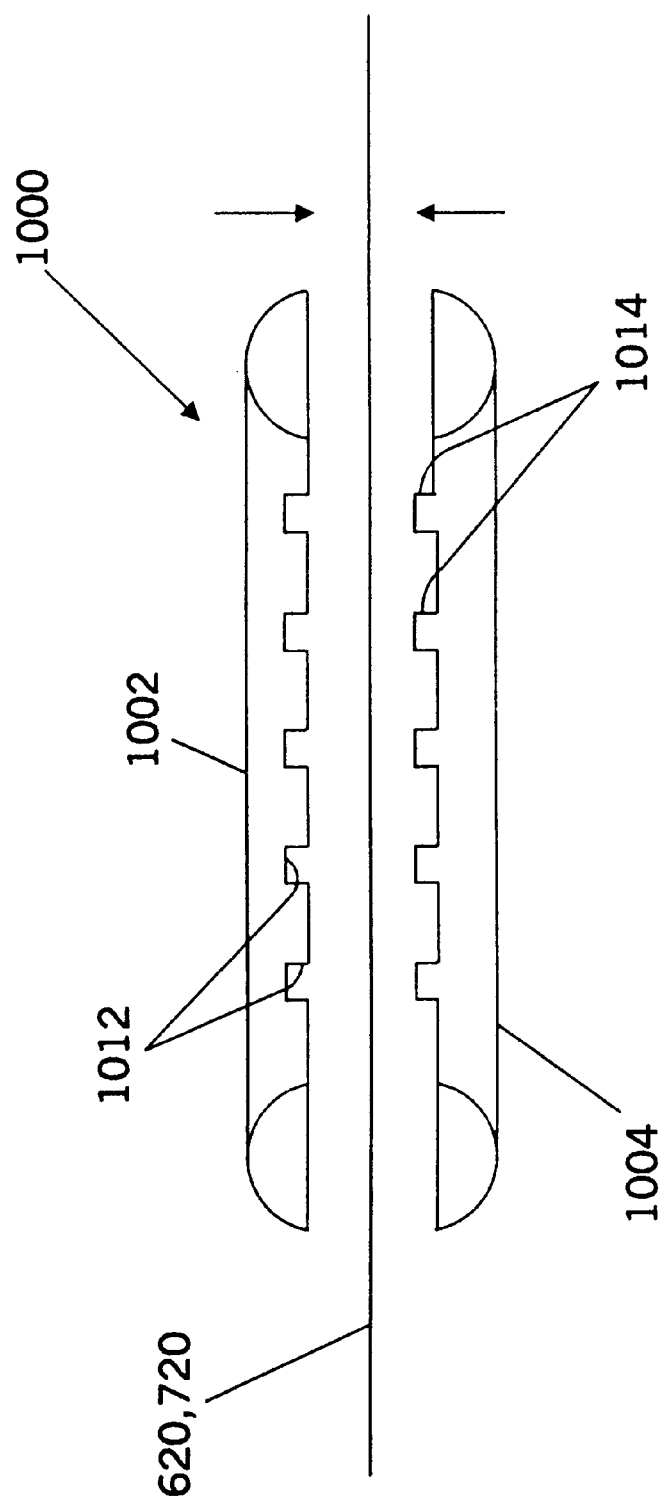

VAGINAL DEVICE

CROSS REFERENCE TO RELATED APPLICATION

This application is a continuation in part of Ser. No. 08/960,898 filed Oct. 30, 1997 now U.S. Pat. No. 5,819,742. Ser. No. 08/960,898 claims the benefit under Title 35, United States Code §119(e) of U.S. Provisional Patent Application Serial No. 60/030,361, filed Nov. 6, 1996.

GOVERNMENT LICENSE RIGHTS

The invention claimed herein was made under U.S. Agency for International Development Contract No. CCP-A-OO-95-00022-02, and the U.S. government has certain rights therein.

FIELD OF THE INVENTION

The invention relates to a vaginal device that may be used to provide physical and chemical barriers to contraception or protection against sexually transmitted diseases (STDs), or both. The vaginal device may also be used to treat vaginal conditions such as bacterial vaginosis, or to deliver medications intended for systemic administrations.

BACKGROUND OF THE INVENTION

Vaginal sponge contraceptives have gained favor as a single-use contraceptive providing a physical barrier to sperm entry to the cervical canal as well as a chemical barrier due to a chemical spermicidal agent typically included in the sponge. Vaginal sponges are formed of compressible polyurethane foam or other plastic foam material in the shape of a sphere, disc or doughnut. The sponge, when inserted into the vagina to cover the cervical area, has the ability to absorb sperm and block passage of sperm to the cervical canal. Additionally, spermicide may be released from the sponge to create the mentioned simultaneous chemical barrier. Disadvantages of the sponge include its expense and its large size and resultant bulky packaging requirements. Also, in its usual application, the sponge does not provide material protection against transmission of STDs.

The well-known diaphragm method of female vaginal contraception provides a physical barrier to passage of sperm to the cervical canal. The diaphragm is also used in association with spermicides. A major disadvantage of the diaphragm is the need for careful and accurate placement of the device so that it properly covers the cervix. In addition, because of the nature of diaphragms, they are unable to retain spermicidal agents except in the concave side of the "dome" diaphragm.

While the sponge and diaphragm, as well as other physical barrier female contraceptive devices such as the cervical cap, provide relatively reliable blockage of sperm to the cervical canal, and these devices may be used with spermicides, there is a need for a reliable, highly effective, low cost barrier contraceptive method that addresses the above mentioned disadvantages of the sponge and diaphragm while providing protection against both pregnancy and STDs.

SUMMARY OF THE INVENTION

In one basic aspect, the present invention may be defined as a vaginal device including a towelette formed of sheet material sized to fit within the vagina of a human female, and a preventive or therapeutic formulation incorporated into the towelette. As used herein, the term "preventive formulation" designates the active chemical agents that may be used with this device as a barrier to contraception, or as protection against sexually transmitted disease, or both. The preventive formulation may include one or more pharmacologically active agents. The preventive formulation may also include other additives well known to those in the pharmaceutical industry, whose purpose may be to aid in the preservation of the active agents, or to improve the functionality or acceptability of the product. The term "therapeutic formulation" refers to medications for treatment of vaginal conditions such as vaginal candidiasis, trichomoniasis and bacterial vaginosis, as well as medications that may be delivered by the present invention for systemic administration. Thus, vaginal devices of the invention may be referred to herein as incorporating a preventive formulation or a therapeutic formulation or simply a formulation.

The vaginal device may be provided with means, hand-engagable by a female user, for facilitating removal of the device. The removal means may take the form of a hand-engagable structure at the peripheral edges of the towelette, a string, or a ring that is inserted with the device. Preferably, the towelette sheet material is a nonwoven fabric that has the ability to carry approximately 1 to 10 ml of gel. Preferred materials include polyester and polyester/cotton blends. Such fabrics may permit printing of instructions for use on the device itself.

In certain embodiments, the vaginal device may include a flexible ring having an outside diameter that is preferably between about 50 mm to 70 mm. Most preferably, the ring is affixed to the towelette to define a dome-shaped towelette portion on one side of the ring and a depending skirt on the other side. This device may be inserted into the vagina of a human female with the dome portion thereof covering the cervix. The dome-and-skirt towelette may be formed by folding a blank sheet of material according to techniques described herein.

BRIEF DESCRIPTION OF THE DRAWINGS

Some of the objects having been stated, other objects will appear as the description proceeds, when taken in connection with the accompanying drawings, in which

FIG. 6 is a top view of a third vaginal device of the invention incorporating a folded towelette and an affixed support structure in the form of a ring.

FIG. 7 is a sectional view of the towelette of FIG. 6 taken along the line 7—7.

FIG. 8 is a top view of a fourth vaginal device of the invention that includes a towelette having a pocket that holds a support structure in the form of a reusable ring.

FIG. 9 is a sectional view of the towelette of FIG. 8 taken along the line 9—9.

FIG. 13 is a pictorial view of a unitary vaginal device having a flexible ring joined to appropriate sheet material to define a dome and depending skirt. While FIG. 13 shows a depending skirt, which is large in relation to the ring, the depending skirt may be quite small, e.g. extending only 1 cm beyond the ring.

FIG. 16B shows the blank of FIG. 16A after folding.

FIG. 17 is a pictorial view of a ring suitable for use in connection with the vaginal devices of FIGS. 13 and 14.

FIGS. 18A, 18B, 18C and 18D depict alternative cross-sectional configurations for the ring of FIG. 17.

FIG. 19 is a view of a "split ring", the two halves of which may be snap-fitted together with the towelette sheet material therebetween for the purpose of forming a unitary dome-and-skirt towelette configuration with attached ring.

DETAILED DESCRIPTION OF THE INVENTION

While the present invention will be described more fully hereinafter with reference to the accompanying drawings, in which aspects of the preferred manner of practicing the present invention are shown, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

Figure 1:
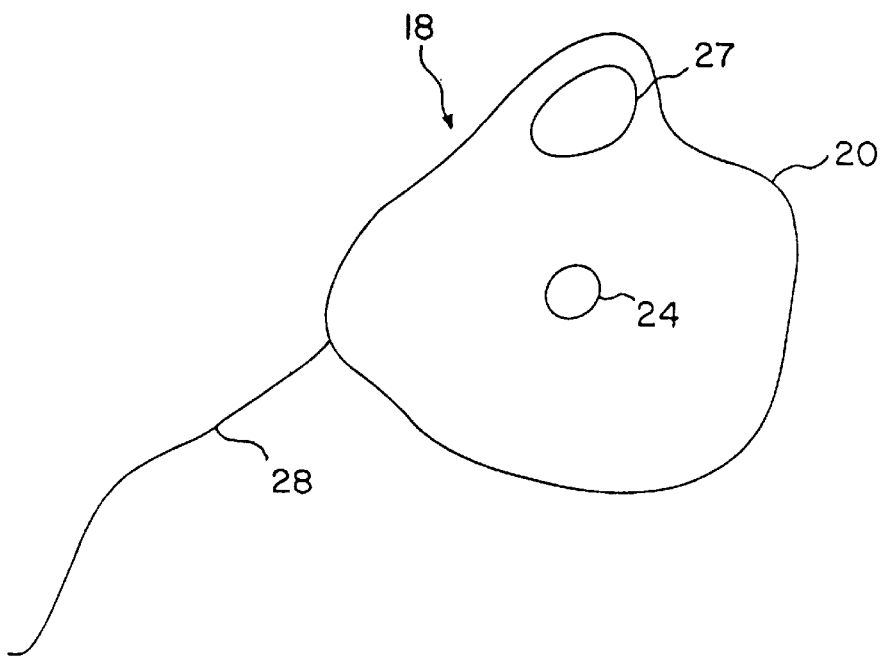
FIG. 1 is a top view of a vaginal device of the invention including a towelette containing a preventive or therapeutic formulation.

Referring to the drawings and particularly to FIG. 1, there is shown a first embodiment of a vaginal device 18 that will be discussed primarily with reference to use for contraception and preventing the transmission of sexually transmitted diseases, with the understanding that this and other embodiments may be used with appropriate formulations to treat vaginal conditions such as vaginal candidiasis, trichomoniasis or bacterial vaginosis, as well as to deliver medications intended for systemic administration. Device 18 includes a towelette 20 that takes the form of a piece of absorbent, crushable, tear resistant sheet material which may be similar to the sheet material forming commonly used hand wipes or baby wipes. More particularly, the towelette may be made of a nonwoven fabric. The fabric should be strong (able to withstand an 8–10 lb. force before failure in either direction). The material should have the appropriate properties of absorbency, penetration, and retention to carry a minimum of 5 milliliters of gel. While carrying by absorption is preferred and referred to primarily herein, carrying by adsorption may be used with appropriate towelette materials and formulations and is considered equivalent to absorption. Preferably, the material is biodegradable or disposable by burning. Preferred materials include polyester, or polyester/cotton blends. An advantage of using polyester is the possibility of using thermal bonding. Many of the materials suitable for towelettes of the present invention are well known to those skilled in the art. The towelette can be made from many of the same materials which are suitable for use as a moist wipe, including meltblown, coform, air-laid, bonded-carded web materials, hydroentangled materials and the like and can comprise synthetic or natural fibers or combinations thereof. The towelette may have a basis weight of from about 25 to about 120 grams per square meter and desirably from about 40 to about 90 grams per square meter.

Towelette 20 may have any desired shape such as square, rectangular, oval or circular, with either smooth or scalloped edges. When laid flat, the surface area of towelette 20 may range from approximately 9 to 36 square inches. This total area has been found suitable for the towelette to carry an effective amount of preventive formulation, and for the towelette to be crushed into a round disc-like shape during intercourse.

Towelette 20 is moistened with a flowable preventive formulation that may be liquid, cream or gel, and which may also have lubricating and/or foaming qualities. In certain embodiments, the foaming property of a chemical agent such as hydrogen peroxide (that may be located between the folds or between two thicknesses of the towelette) may be used to cause the towelette, during intercourse, to cause the towelette, after insertion into the vagina, to increase in volume and to become a more effective physical barrier. A foaming agent such as hydrogen peroxide may also be used to enhance diffusion of the preventive formulation within the vagina.

Figure 4:
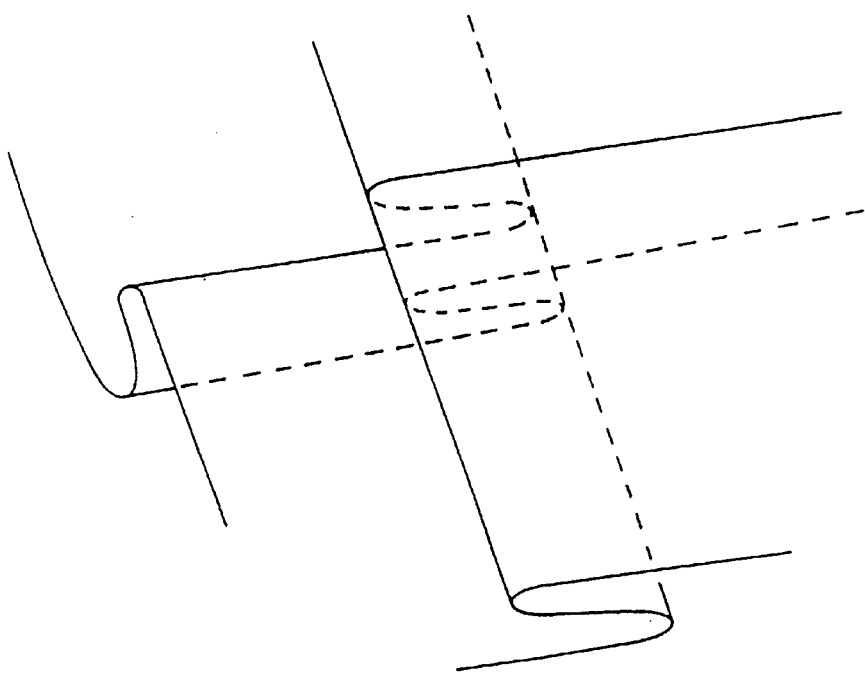
FIG. 4 is an enlarged detailed view of a portion of a towelette showing the folds made in the manufacturing process to provide reservoir-like spaces for holding an amount of protective formulation beyond that which can be absorbed into the towelette material.

Towelette 20 includes an optional spermicide reservoir 24 located approximately in the middle of the towelette so that a larger volume of the preventive formulation may be delivered into the vagina than is absorbed by the towelette itself. Reservoir 24 may consist of a separately formed volume as shown in FIG. 1. A reservoir may also be formed by a space between layers of the towelette created by folding the towelette (FIG. 4), or simply by the space between the folds of the wipe, without any special folding or other provisions for the spermicide.

A removal means in the form of a length of string 28 is attached to towelette 20 so that the towelette can be easily removed after intercourse. A supplemental removal means in the form of perforation 27 may also be provided.

Figure 2:
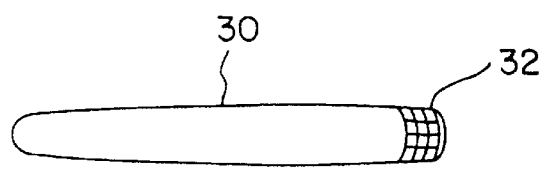
FIG. 2 is a pictorial view of an inserter that may be used to insert the towelette into the vagina.

An inserter 30 (FIG. 2) may be optionally used to assist in inserting towelette 20 and string 28 into the vagina. In its illustrated form, inserter 30 is a smooth, blunt-ended device approximately 5 to 8 inches in length. Inserter 30 may include a hook 32 on one end to facilitate removal of the towelette. Depending on a woman's preference, she may insert the towelette using her finger or an inserter.

Towelette 20 may be folded and individually packaged in small moisture-proof packets 34 (FIG. 3) similar in size and composition to packets containing conventional cleaning wipes or condoms.

The preventive formulation of the device may consist of nonoxynol-9 gel, or may be made of any agent, new or existing, appropriate for such use. Potential agents which may be used with this invention include, but are not limited to: hydrogen peroxide, carbamide peroxide, benzalkonium chloride, various types of monoclonal antibodies, C-31G (a formulation being developed by BioSyn, Inc.), cholates and desoxycholates, Buffer-Gel (a formulation being developed by ReProtect, Inc.), chlorhexidine, and sulfated or sulfonated polymers of various types (e.g. dextran and carrageenan).

The towelette of the invention may be inserted into the vagina either immediately before, or up to several hours before intercourse, and protects the user from pregnancy or from certain sexually transmitted diseases, or both.

During intercourse, the penis will rub and push against the towelette. In some cases, the motion of the penis will compress the towelette into a crumpled disc in the upper vagina to give a physical barrier.

With respect to the prevention of sexually transmitted diseases, the preventive formulation disposed on the towelette may be spread over the anatomical surface of the vagina during insertion of the towelette to provide temporary but effective protection against certain STDs.

The volume of the preventive formulation delivered to the vagina by the towelette may be on the order of about 1 ml to about 10 ml.

Figure 5:
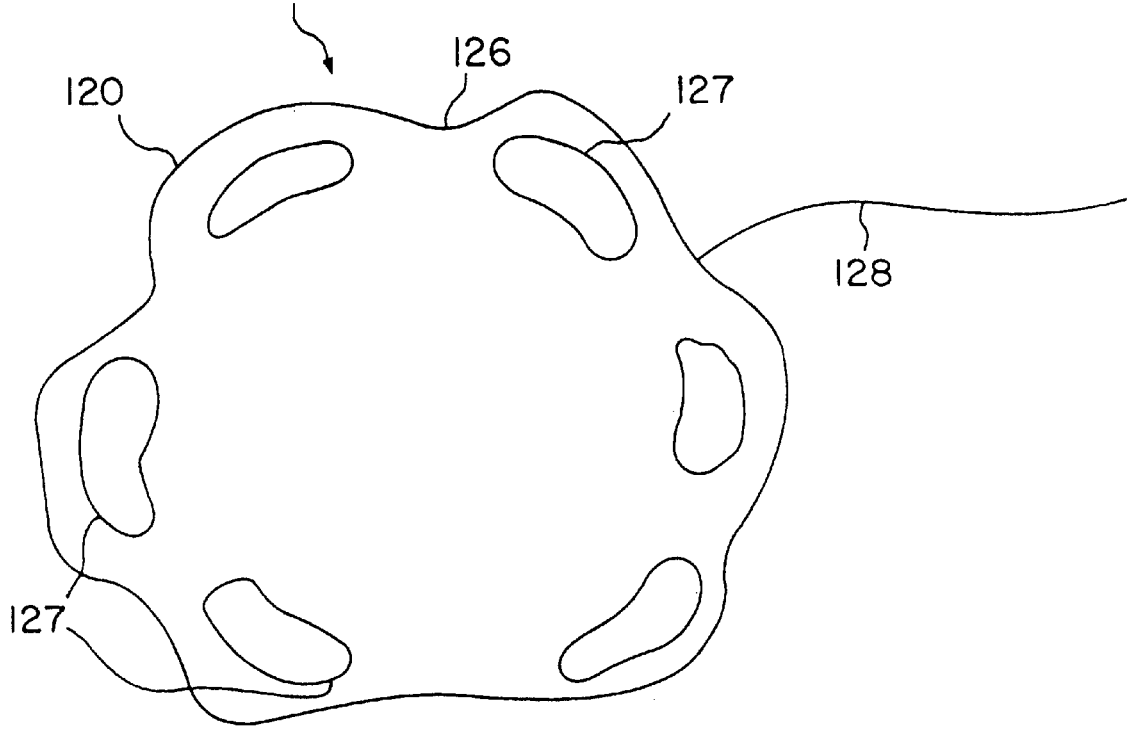
FIG. 5 is a top view of a second vaginal device of the invention.

Referring now to the embodiment of FIG. 5, device 118 includes a towelette 120 that is formed of sheet material similar to that of towelette 20 of FIG. 1. Towelette 120 is moistened with a preventive formulation in the form of a flowable spermicidal and/or microbicidal composition which may be a liquid, cream or gel, in the same fashion as towelette 20, with or without the optional reservoir.

Towelette 120 includes a central portion 122 without perforations, and has a scalloped outer rim 126 with multiple perforations 127 so that it resembles a lace doily. The towelette may be colored to further improve aesthetic appeal. In addition to the aesthetic feature provided by perforations 127, the perforations have a functional purpose in that the towelette may be removed from the vagina by a finger engaging and catching a perforation. Additionally, towelette 120 may be provided with a removal means in the form of a string 128.

The description will now turn to a discussion of several additional embodiments of the invention that include a rigid or semi-rigid support structure that is inserted into the vagina along with the towelette. More specifically, each of the embodiments illustrated in FIGS. 6–14 includes a support structure in the form of a ring that is used to assist in removal of the towelette following intercourse. The ring also serves to assist in (i) spontaneous positioning of the towelette so that it covers the cervix and (ii) maintaining the shape of the towelette during intercourse. In all embodiments illustrated in FIGS. 6–14, the ring is formed of a soft flexible material. The softness of the material, as measured by a durometer, preferably will not be less than about Shore A 35 or greater than about Shore A 70. Tear strength values of the preferred ring materials are in the range of 5 to 10 lbs., as measured by a pull test. Preferred materials are able to withstand an 8 to 10 lb. pull before failure.

Biocompatibility of the ring material is based on blood/material interaction data, animal implant testing, and cytotoxicity testing. Preferred materials are biocompatible and elastomeric at body temperature. Also, preferred materials lack the addition of chemicals that lead toward leachable material, and the materials preferably are chemically resistant so that they do not degrade when exposed to low concentrations of various solvents.

The preferred ring materials are typified by silicone elastomer, diisocyanates (exemplified by polyurethane elastomer or silastic polyurethane), styrene-butadiene block co-polymers (for example GLS Kraton) and ethylene vinylacetate copolymers. The types of processing for forming the ring may include liquid injection molding, liquid castable, or pellet injection molding. Other materials may be used if formulated to high standards. These materials include, but are not limited to, acrylate-butadiene, bromoisobuteneisoprene, butadiene, chlorinated polyethylene, chloroisobutene-isoprene, chloropene, chlorosulfonated polyethylene, chlorotrifluoroethylene-vinyllidene fluoride, epichlorohydrin (homo- and co-polymer), ethylene-propylene copolymer, terpolymer, fluorosilicone, isobutene-isoprene, isoprene, nitrile-butadiene, nitrile-chloroprene, nitrile-isoprene, polyacrylate, pyridine-butadiene, pyridine-styrene-butadiene, styrene-chloroprene, and styrene-isoprene.

The ring is appropriately sized to achieve the desired function, with a ring size having an outside diameter of approximately 50–70 mm and a cross sectional diameter of approximately 2–10 mm being preferred. The ring may be disposable with the towelette after intercourse, in which case the ring is preferably permanently affixed to the towelette, or the ring may be reusable, in which case the ring may fit into a pocket in the towelette or otherwise be separable from the towelette after intercourse.

It will be appreciated that the mentioned ring is one preferred form of a rigid or semi-rigid support structure to be used in conjunction with the towelette. Other forms for the support structure, such as a ball, disc or a multifaceted cube, may be used.

Referring to FIGS. 6 and 7, device 218 includes a towelette 220 formed of absorbent fibrous material as described above. Towelette 220 is folded at fold line 221 to create opposing towelette faces 225, 226. A ring 229 as described above is placed between opposed faces 225, 226 and the faces are spot bonded together within the ring at 231 to affix the ring to the towelette. The spot bonding may be achieved by heat sealing, adhesives, or other suitable means. The ring support structure is used to facilitate insertion of the towelette, to facilitate appropriate positioning of the towelette so that it may serve as a physical barrier during intercourse, and to facilitate removal of the towelette after intercourse. It is contemplated that the ring in this embodiment be disposable along with the towelette.

While towelette 220 of FIGS. 6 and 7 is formed from a single sheet of material with a fold line, two opposed sheets may be used, with the two sheets being joined together into a unitary towelette by the spot bond.

FIGS. 8 and 9 illustrate another device 318 of the invention wherein the sheet material of towelette 320 is folded upon itself along a fold line 321 to create opposed towelette faces 325, 326. The edges of the towelette at 327, 328 are then joined or sealed by suitable means, for example, an adhesive, thermal bonding or stitching, to form a pocket 333 bounded by fold line 321 and sealed edges 327, 328. Prior to insertion of towelette 320 into the vagina, a ring 329 as described above is inserted into pocket 333. In this embodiment the ring serves the same functions as described above in connection with the previous embodiment. After intercourse, the ring and towelette are removed together. Because the ring is separable from the towelette, it may be reused after washing.

Figure 3:
FIG. 3 is a pictorial view of a package, similar to a conventional package for condoms or cleaning wipes, for packaging the device of FIG. 1.

The towelette of the embodiment of FIGS. 8 and 9 may be packaged by itself in folded fashion in a package as shown in FIG. 3. The towelette is simply removed from the package, unfolded to expose the opening to pocket 333, and the ring is inserted into the pocket. The towelette and ring are then inserted into the vagina before intercourse. After intercourse, the towelette and ring are removed by simply grasping the ring.

Figure 10:
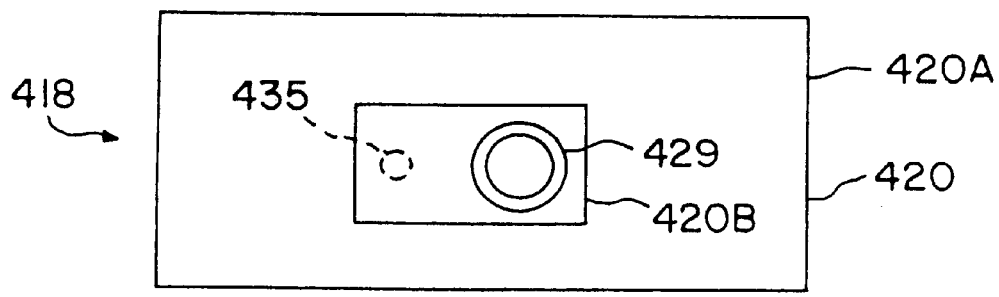
FIG. 10 is a top view of a fifth vaginal device of the invention.

FIG. 10 illustrates another device 418 of the invention including a towelette 420. Towelette 420 includes a first large sheet 420A that is spot bonded at 435 to a second smaller sheet 420B. A ring 429 is fixedly secured to the smaller sheet by adhesive or other suitable means. This embodiment is used in the same fashion as the embodiment of FIGS. 6 and 7 with the ring preferably being discarded along with the towelette after use.

Figure 11:
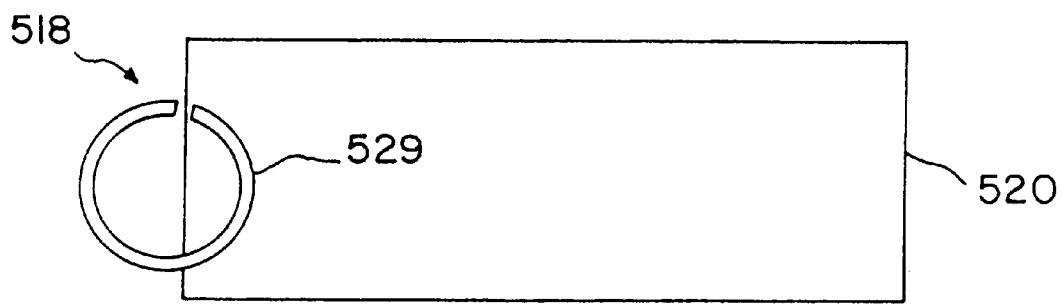
FIG. 11 is a top view of a sixth vaginal device of the invention including a reusable snap-on ring that is removably attached to the towelette.
Figure 12:
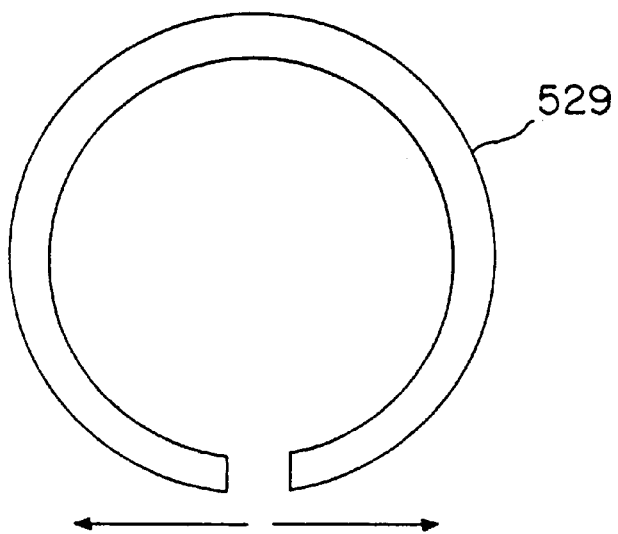
FIG. 12 is an enlarged view of the snap-on ring of FIG. 11.

FIG. 11 illustrates yet another device 518 wherein the towelette 520 is a single sheet and the ring takes the form of a reusable snap-on ring 529. As shown in FIG. 12, ring 529 may be opened by application of outwardly directed force in the direction of the arrows so that the towelette may be placed therebetween and then secured to the ring when the force is released.

Figure 13:
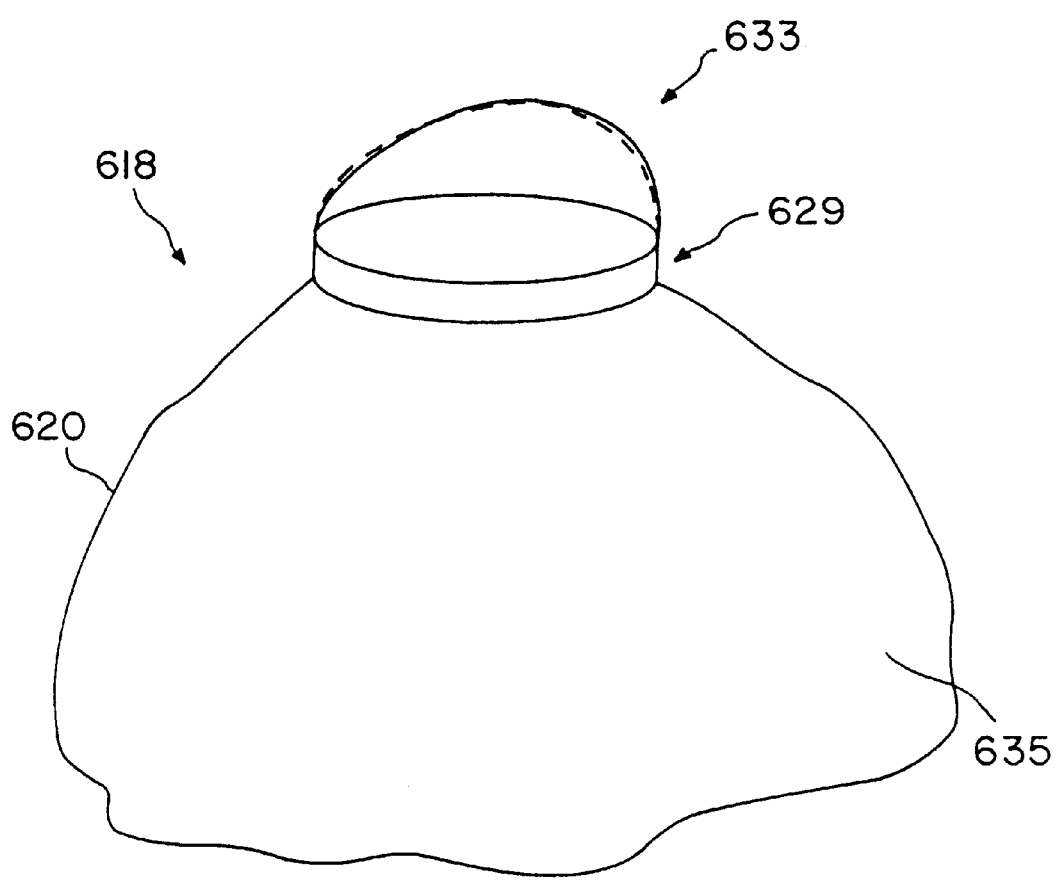

FIG. 13 illustrates another device 618 having a towelette 620 joined to a flexible ring 629 to form a unitary structure defining a dome 633 and a depending skirt 635. The material for the towelette may be as described above in connection with other embodiments. Alternatively, the ring 629 and towelette 620 may be formed as a single unit of absorbent material, for example, a suitable polymer material such as polyurethane foam or polyvinylalcohol foam. A preferred way to form ring 629 and towelette 620 of this material is by liquid injection molding. The pore size, density, percent of open cells, and the chemical properties of the material can be controlled and varied, by those skilled in the art, to meet design goals, including the ability to carry the desired amount of active agent.

Figure 14:
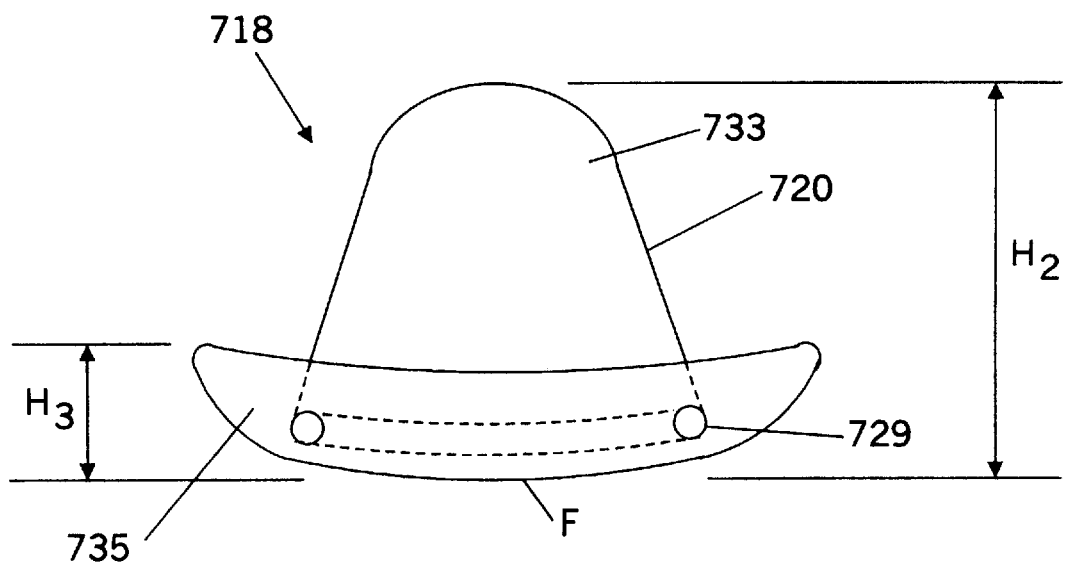
FIG. 14 shows a vaginal device similar to the device of FIG. 13 but with a shorter depending skirt that is folded up so that the dome and skirt portions of the device, along with the cojoined ring thereof, present a "sombrero" configuration.

FIG. 14 shows another vaginal device 718, similar to the device of FIG. 13, wherein a flexible ring 729 is attached to the towelette 720 to define a dome portion 733 and a depending skirt 735. According to this embodiment, skirt 735 is relatively short, e.g. 25 mm, and is folded upwardly below the ring at F to create a "sombrero" configuration.

As discussed above, it will be appreciated that the rings assist in positioning the vaginal devices. In this regard, the ring support structure, and particularly the ring support structure used in association with cojoined dome-and-skirt towelette material as shown in FIGS. 13 and 14, facilitate the spontaneous positioning of the device around the cervix. Instructions for use of the vaginal devices of FIGS. 13 and 14 do not require that the woman feel her cervix. The woman simply inserts the device deeply into the vagina. The ring shape of the support structure typically will lead to spontaneous positioning of the ring structure around the cervix, so that the cervix is covered by the dome-shaped portion. In this regard, the cervix protrudes into the vagina in a hemispherical shape. Preferably, the size of the ring is large enough so that the cervices of a vast majority of women will fit within the ring. Thus, the ring-shaped support structure will facilitate the persistent positioning of the vaginal device over the cervix before, during and after sexual intercourse. With respect to sizing of the ring of FIGS. 13 and 14, ring sizes having an outside diameter of approximately 50–70 mm and a cross-sectional height $H_1$ (FIG. 17) of approximately 2–10 mm are preferred.

In one particular embodiment of the device of FIG. 14, the outside diameter of ring 729 is approximately 63 mm, the height $H_1$ of the ring is approximately 3 mm, the total height $H_2$ of the device, after upwardly folding the skirt material at F, is in the range of approximately 20 mm to 80 mm, preferably about 50 mm, and the height $H_3$ of the folded-up skirt portion is in the range of approximately 10 mm to 40 mm, preferably about 20 mm.

Figure 15A:
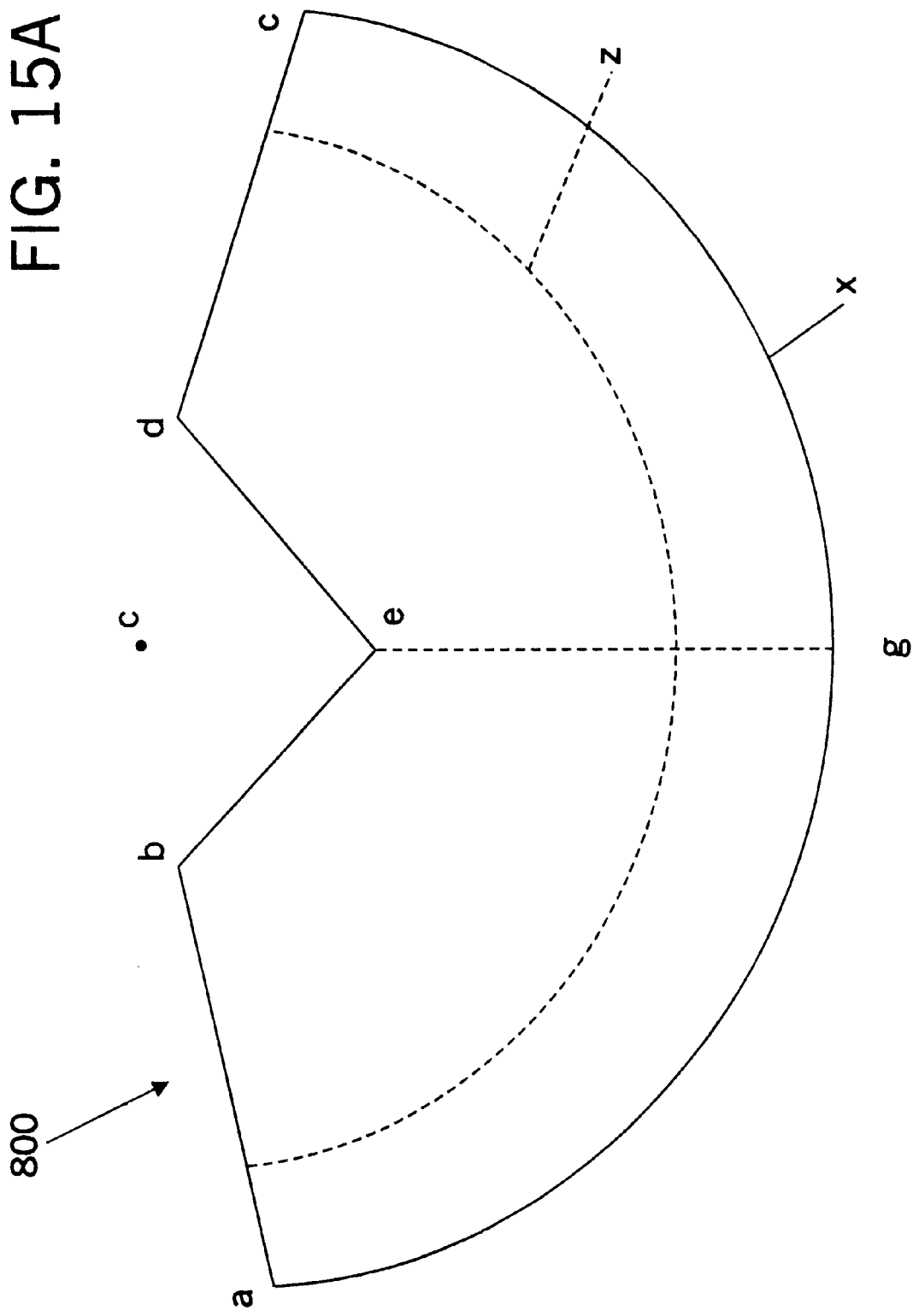
FIG. 15A is a top view of a blank of sheet material that may be used to form the vaginal device of FIG. 14.
Figure 15B:
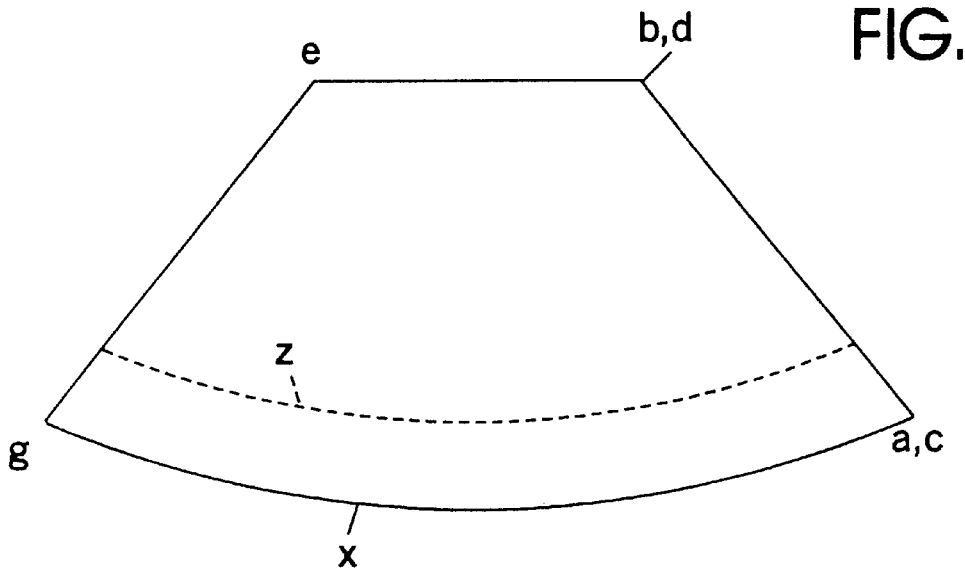
FIG. 15B is a pictorial view showing the blank of FIG. 15A after folding at fold line e–g and then sealing or otherwise joining the edges a–b/c–d and b–e/d–e to form a dome-and-skirt towelette to which a ring may be joined.
Figure 15C:
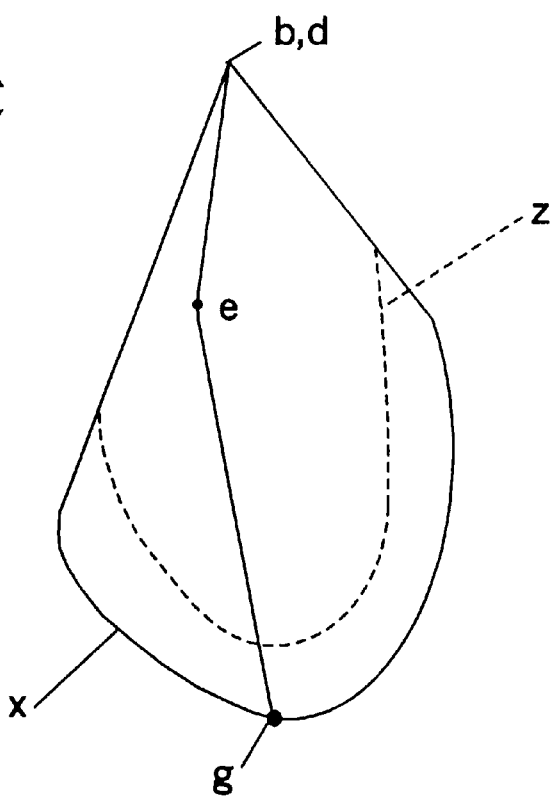
FIG. 15C shows the towelette of FIG. 15B expanded so that it assumes its dome shape.

FIG. 15A illustrates a blank of absorbent sheet material for forming the dome-and-skirt towelette configuration of the vaginal device illustrated in FIG. 14. Blank 800 includes a curved base portion X that terminates at points a and b where radial edges a–b and c–d extend inwardly toward the center of curvature C of base X. A pair of inwardly projecting edges b–e and d–e join together at point e. Blank 800 is symmetrical about a fold line e–g and, when folded thereabout, brings edge pairs a–b/c–d and b–e/d–e together into overlying orientation. FIG. 15B shows the edge pairs joined by appropriate sealing with adhesive, by heating, stitching or the like to create the dome-and-skirt towelette form to which the ring 729 may be attached along line Z. FIG. 15C shows the towelette expanded so that it assumes its dome shape.

Ring 729 may be attached to the sheet material in various ways. It may be attached by bonding, using appropriate adhesives or by stitching or by heating. In the case of heating, various means may be used to apply heat to melt either the ring material or the towelette sheet material for attachment.

In one particular embodiment specifically adapted for producing a vaginal device as shown in FIG. 14, the curved base X of blank 800 subtends an arc of approximately 110° to 180°, with an arc of approximately 150° being preferred. The radius of curvature of curved base portion may be in the range of approximately 60 mm to 150 mm, with approximately 90 mm being preferred. In this preferred embodiment, edges a–b and c–d are on the order of 70 mm and, edges b–e and d–e are on the order of 30 mm with the adjoinment line Z for ring 729 being located approximately 20 to 25 mm inwardly from the curved base portion X. The preferred material for the towelette of this embodiment is a nonwoven fabric which is a combination of rayon and polyester materials.

Figure 16C:
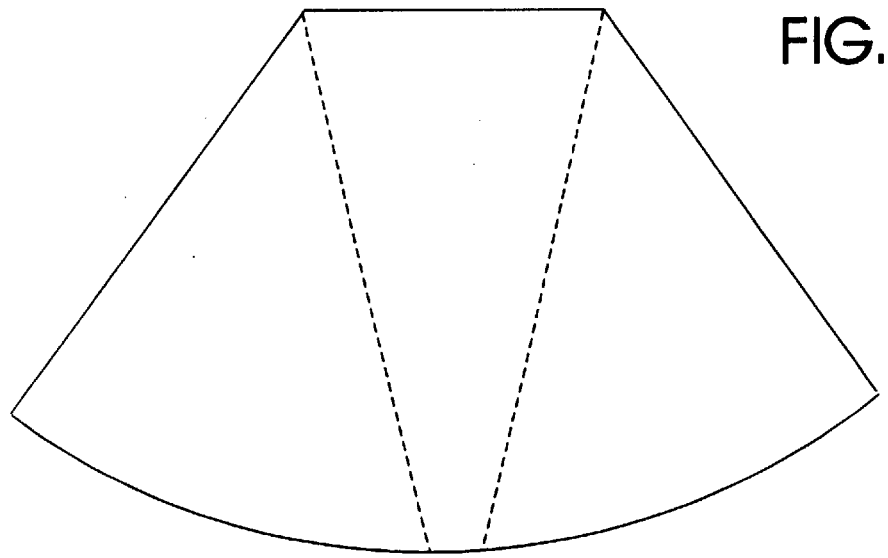
FIG. 16C shows the final dome-and-skirt configuration formed by the blank of FIGS. 16A and 16B after trimming of excess material.
Figure 16A:
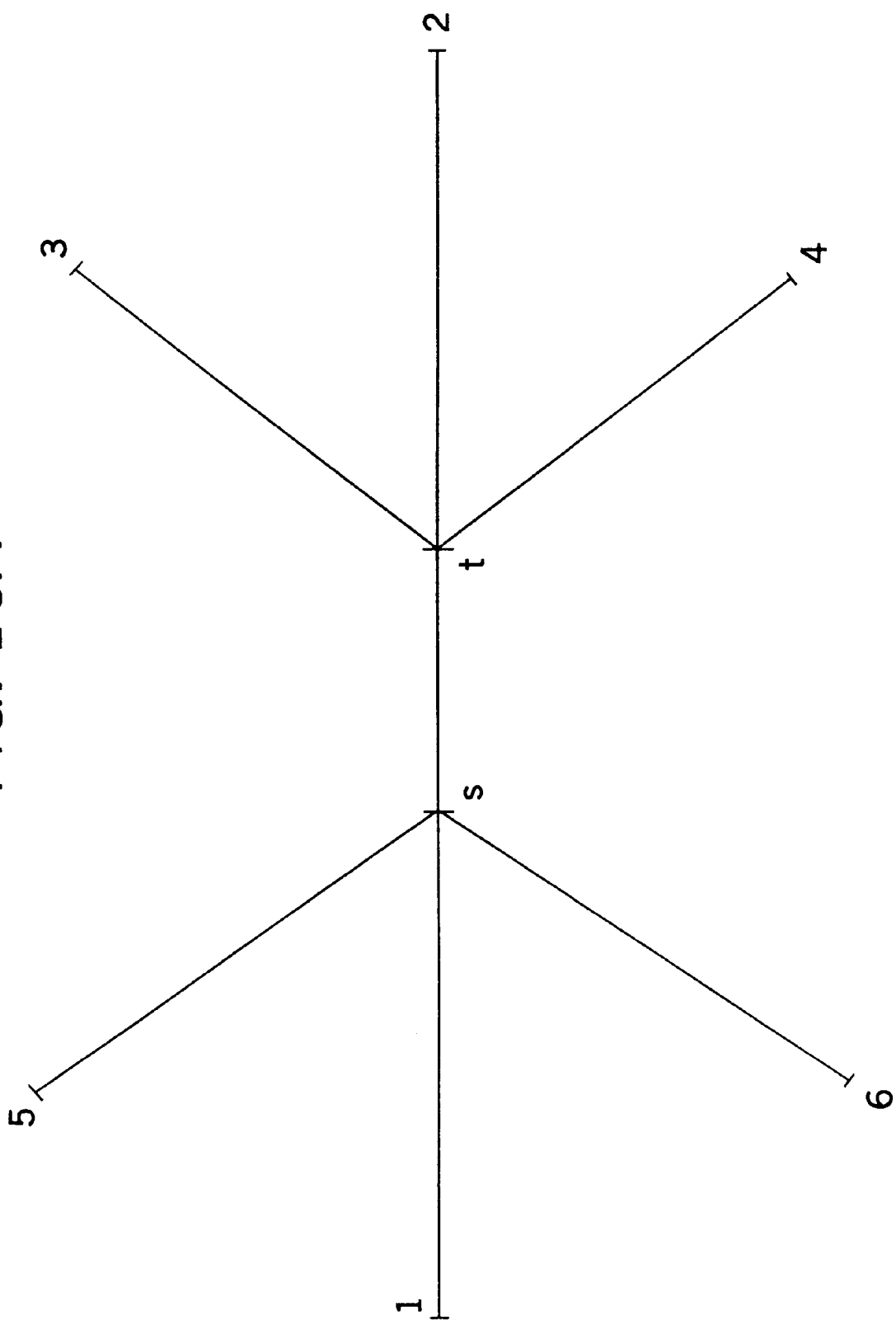
FIG. 16A is a top view of a sheet of towelette material having fold lines about which the sheet may be folded to create a dome and skirt configuration without the necessity of sealing or otherwise joining edges together.

FIG. 16A is a top view of a sheet of towelette material having fold lines about which the sheet may be folded to create a dome and skirt for a vaginal device of FIG. 13 or 14 without the need of sewing or otherwise joining together edges of material. Sheet member 900 will be described, along with the folding thereof, as having folds that are acute or obtuse with respect to the inside of the dome that is ultimately formed thereby. In this regard, an acute fold is a fold that has a more acute angle, i.e., less than 180°, with respect to the inside of the dome, an obtuse angle is more than 180°. Using this definition, folds s-b, s-5, s-6, t-3 and t-4 are acute folds. Folds s-1 and s-2 are obtuse folds. This method of folding leaves the excess folded material on the inside of the dome. After the rectangular sheet 900 is folded as described above, it has the appearance shown in FIG.

16B. The lower edge e is thereafter trimmed in a singular operation in a circular arc to provide the dome-and-skirt configuration with a curved-shaped lower border as shown in FIG. 16C.

Referring back to FIG. 16A, an alternative folding means which will leave the folded excess on the outside of the dome is as follows: first, fold along axis 1–2, then fold along axis t-3/4 in one fold, and along axis s-5/6 in one fold. As previously described, the lower edge of the so folded material is trimmed to produce a dome-and-skirt configuration with a curve-shaped lower border defining the end of the skirt.

FIG. 17 is a pictorial view of a ring suitable for use with the present invention, particularly with respect to the dome/skirt embodiments of FIGS. 13 and 14. It will be appreciated that the ring may be of a specific profile (i.e., cross-sectional configuration) to add one-dimensional stiffness to the device in order to facilitate insertion. Thus, in addition to a cross-sectional profile that is circular, as shown in FIG. 18A, alternative cross-sectional profiles that are oval (FIG. 18B), rectangular (FIG. 18C) or rectangular with rounded corners (FIG. 18D) may be utilized. A ring with a circular profile will tend to be equally flexible in all directions. The advantage of an oval or rectangular ring profile is that the ring is less flexible in one plane or dimension. This one-dimensional stiffness makes the device easier to insert. In addition to the oval or rounded rectangular profile giving the support structure a small amount of rigidity in one dimension, these configurations also provide a relatively flat surface that is more conducive to grasping between two fingers, thus making it easier to insert.

The ring may be attached to the towelette sheet material in various ways. The ring may be attached by bonding, using various adhesives, or stitching or heating. In the case of heating, various means may be used to apply heat to melt either the ring or the membrane for attachment.

Referring to FIG. 19, a "split ring" design may be used to facilitate attachment of the ring to the towelette sheet material, particularly sheet material 620, 720 of FIGS. 13 and 14. Split ring 1000 preferably is formed of suitable plastic material and comprises an upper female portion 1002 and a lower male portion 1004. Members 1002, 1004 effectively form a ring that is split much as a sliced bagel. Upper portion 1002 includes multiple recesses 1012 that mate with projecting pins 1014 on the lower portion 1004. In assembly of the vaginal device, the towelette material of the dome/skirt device of FIG. 13 or 14 is placed between the ring halves at the appropriate positioning defining the line of demarcation between the dome and skirt, and thereafter the two ring halves are joined together by frictional engagement or snap fitting with the towelette sheet material captured therebetween. This split ring structure avoids the need for the use of more complex and time consuming means of ring attachment, such as adhesives or heat. It will be appreciated that the openings in upper member 1002 preferably may be narrower at their entrance than the widest part of the pins. Thus, when the pieces are forced together, the intrinsic flexibility of the plastic will permit the larger piece to penetrate the smaller entrance to the hole. However, once assembled, the two pieces will be difficult to separate.

It will be appreciated that one primary utility of the present invention is related to preventing conception or the transmission of sexually transmitted diseases, or both. Additionally, vaginal devices of the invention may be used for the efficient delivery of medications for the treatment of vaginal conditions such as vaginal candidiasis, trichomoniasis and bacterial vaginosis. For example, Metrogel-Vaginal®, produced by 3M Pharmaceuticals is used for the treatment of bacterial vaginosis. It is recommended for use once or twice daily. The active ingredient is metronidazole, 0.75%. The medicine is given as 5 grams of a gel in a vaginal applicator. One common complaint that women have about such formulations is that the gel leaks from the vagina. The vaginal device of this invention may be used instead of a gel applicator to deliver this medication, and to help keep the medication in the vagina. Instead of a gel applicator, approximately the same amount of medication may be delivered to the vagina using the present device, with less leakage of the medication from the vagina. In addition, a single daily application of the medication used with the present device will be just as effective as giving two doses of plain gel per day.

Numerous studies have shown that the vagina absorbs some medications as effectively as, or sometimes more effectively than, the gastrointestinal tract. Thus, the vaginal device of this invention may also be used to deliver medications intended for systemic administration.

While the invention has been described in connection with certain illustrated embodiments, it will be appreciated that modifications may be made without departing from the true spirit and scope of the invention.

That which is claimed is:

1. A vaginal device comprising:
   a towelette formed of sheet material sized to fit within the vagina of a human female;
   a ring joined to said towelette; and
   an effective amount of a preventive or therapeutic formulation incorporated into said towelette.

2. The vaginal device of claim 1 wherein said ring is joined to the towelette to define dome and depending skirt portions of towelette material.

3. A vaginal device according to claim 2 wherein said ring and towelette are separate elements that are secured together to form a unitary device.

4. A vaginal device according to claim 2 wherein said ring and towelette are formed as a single unit of absorbent material.

5. A vaginal device according to claim 4 wherein said sheet material comprises a polymer material.

6. A vaginal device according to claim 5 wherein said polymer material is selected of the group consisting of polyurethane foam and polyvinylalcohol foam.

7. A vaginal device according to claim 2 wherein the depending skirt extends a distance greater than about 1 cm from the ring.

8. A method of providing protection against pregnancy or sexually transmitted disease, or both, comprising inserting a vaginal device according to claim 2 into the vagina of a human female prior to intercourse and permitting the dome portion thereof to cover the cervix.

9. A vaginal device according to claim 2 wherein the depending skirt is folded along a fold line F to form a vaginal device having a sombrero configuration.

10. A vaginal device according to claim 8 wherein the outside diameter of the ring is approximately 50 mm to 70 mm.

11. A vaginal device according to claim 10 wherein the total height $H_2$ of the vaginal device after folding the skirt along fold line F is approximately 20 mm to 80 mm.

12. A vaginal device according to claim 11 wherein the height $H_3$ of the folded-up skirt portion is approximately 10 mm to 40 mm.

13. A vaginal device according to claim 2 wherein the towelette sheet material comprises a blank of sheet material having a curved base X subtending an arc of approximately 110° to 180° and having end points a and b, radial edges a–b and c–d extending radially inwardly from end points a and b of base X, inwardly projecting edges b–e and d–e and a fold line e–g about which the blank is symmetrically disposed and folded with edge pairs a–b/c–d and b–e/d–e joined together.

14. A vaginal device according to claim 1 wherein the formulation is selected from the group consisting of nonoxynol-9, hydrogen peroxide, carbamide peroxide, benzalkonium chloride, monoclonal antibodies, C-31G, Buffer-Gel, chlorhexidine, and sulfated or sulfonated polymers.

15. A method of providing treatment of vaginal conditions comprising inserting a vaginal device according to claim 1 incorporating a therapeutic formulation into the vagina of a human female for a time sufficient to treat the vaginal condition.

16. A method of delivering medication intended for systemic administration to a human female comprising inserting a vaginal device according to claim 1 incorporating a therapeutic formulation into the vagina of a human female for a time sufficient to deliver the medication.

17. A blank of absorbent sheet material useful, in association with a cojoined ring, to form a vaginal device having dome and depending skirt portions separated by the cojoined ring, said blank comprising:

a curved base X subtending an arc of approximately 110° to 180° and having end points a and c;

radial edges a–b and c–d extending radially inwardly from end points a and c of base X;

inwardly projecting edges b–e and d–e; and a fold line e–g about which the blank is symmetrically disposed so that, when the blank is folded along fold line e–g, edges a–b/c–d overlie each other and edges b–e/d–e overlie each other.

18. A blank according to claim 17 wherein edges a–b and c–d are approximately 70 mm, edges b–e and d–e are approximately 30 mm and the radius of curvature of base X is approximately 90 mm.

19. A vaginal device comprising:

a towelette formed of sheet material sized to fit within the vagina of a human female; and an effective amount of a therapeutic formulation incorporated into said towelette for treatment of vaginal conditions or delivery of medication intended for systemic administration while the vaginal device resides in the vagina.

20. A vaginal device according to claim 19 wherein said towelette has an area between about 9 to about 36 square inches.

21. A vaginal device according to claim 19 wherein said towelette sheet material comprises an absorbent nonwoven fabric.

22. A vaginal device according to claim 21 including a ring joined to said towelette.

23. A vaginal device according to claim 22 wherein said towelette comprises dome and skirt portions separated by said ring.

* * * * *